United States Patent
Bourissou et al.

(10) Patent No.: US 7,504,524 B2
(45) Date of Patent: Mar. 17, 2009

(54) METHOD FOR SYNTHESIS OF 2,5-DIOXANE-1,4-DIONES

(75) Inventors: Didier Bourissou, Plaisance du Touch (FR); Blanca Martin-Vaca, Toulouse (FR); Frédéric Ben, Toulouse (FR); Magalie Graullier, Toulouse (FR); Roland Cherif-Cheikh, Barcelona (ES); Martin Montes, Sant Quirze Del Valles (ES)

(73) Assignee: Societe de Conseils de Recherches Et d'Applications Scientifiques, Boulogne-Billancourt (FR)

( * ) Notice: Subject to any disclaimer, the term of this patent is extended or adjusted under 35 U.S.C. 154(b) by 0 days.

(21) Appl. No.: 11/572,809

(22) PCT Filed: Jul. 25, 2005

(86) PCT No.: PCT/FR2005/001909

§ 371 (c)(1),
(2), (4) Date: Jan. 26, 2007

(87) PCT Pub. No.: WO2006/018524

PCT Pub. Date: Feb. 23, 2006

(65) Prior Publication Data

US 2008/0004453 A1    Jan. 3, 2008

(30) Foreign Application Priority Data

Jul. 26, 2004    (FR) ................... 04 08211

(51) Int. Cl.
*C07D 319/12*    (2006.01)
(52) U.S. Cl. .................................... 549/274
(58) Field of Classification Search ........... 549/274
See application file for complete search history.

(56) References Cited

FOREIGN PATENT DOCUMENTS

WO    WO2006/018524 A1    2/2006

OTHER PUBLICATIONS

International Search Report for PCT/FR2005/001909.
"Mass Spectra of 18α, 19βH-Ursane Derivatives with a Lactone Arrangement of the Ring E*," Jiří Protiva et al., Collection Czechoslovak Chem. Commun., vol. 46, pp. 1023-1080, 1981 (XP009044327).
"Structure and the Properties of 18α, 19βH-Ursane Derivatives with a Lactone Bridge to Ring E*," Eva Klinotová et al., Collection Czechoslovak Chem. Commun., vol. 45, pp. 1366-1378, 1980 (XP001013529).
Wilson and Jones, "A Recoverable, Metal-Free for the Green Ploymerization of ϵ-Caprolactone," vol. 37, p. 9709-9714 (2004).
Bourissou, et al., "Controlled Cationic Polymerization of Lactide," *Macromolecules*, vol. 38, No. 24 (2005). p. 9993-9998.

*Primary Examiner*—Bernard Dentz
(74) *Attorney, Agent, or Firm*—Hunton & Williams LLP

(57) ABSTRACT

The invention relates to a novel method for the synthesis of 2,5-dioxane-1,4-diones having formula (I), comprising the oxidation of the ketone function of a cyclic compound having formula (II), wherein $R_1$, $R_2$, $R_3$ and $R_4$ independently represent the hydrogen atom, halo, $(C_2-C_6)$ alkenyl, $(C_3-C_7)$cycloalkyl, cyclohexenyl and a radical having formula $-(CH_2)_m-V-W$.

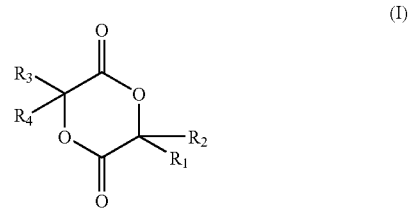

(I)

8 Claims, 1 Drawing Sheet

METHOD FOR SYNTHESIS OF 2,5-DIOXANE-1,4-DIONES

FIELD OF THE INVENTION

The present invention relates to a novel method for the synthesis of 2,5-dioxane-1,4-diones.

BACKGROUND OF INVENTION

PLGAs are generally obtained by ring-opening (co)polymerization of lactide and glycolide. These monomers derived from lactic acid and glycolic acid are the prototypes of 2,5-dioxane-1,4-diones. Modification of the properties of the PLGAs is of great importance, in particular in their use as a biodegradable and bioassimilable matrix for the trapping and controlled release of active ingredients. Somewhat surprisingly, the approach which consists of modifying the substituents of the 2,5-dioxane-1,4-dione backbone has only been slightly developed up to the present, which can in practice be explained by the somewhat low accessibility of these units.

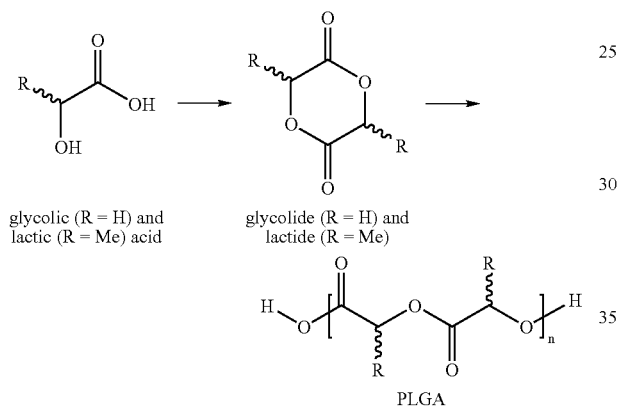

glycolic (R = H) and lactic (R = Me) acid glycolide (R = H) and lactide (R = Me)

PLGA

Symmetrical monomers such a lactide or glycolide are generally prepared from the corresponding α-hydroxy acids. This approach is difficult as it requires the elimination of the water formed and the distillation under vacuum of the monomer. In order to access asymmetrical monomers, two different precursors must be used, typically an α-hydroxy acid and a mono- or di-halogenated derivative (C.-M. Dong et al., *J. Polym. Sci. Part A: Polym. Chem.* 2000, 38, 4179-4184; M. Leemhuis et al., *Eur. J. Org. Chem.* 2003, 3344-3349).

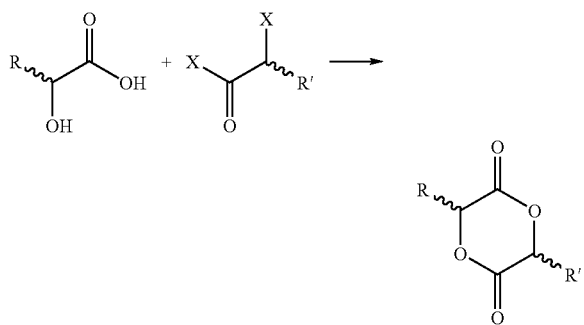

In practice, the major limitation of all these synthesis strategies is probably the final stage of closing the ring with 6 members which is inherently in competition with the formation of dimers and oligomers, by intermolecular rather than intramolecular route. The applicant has therefore envisaged a novel synthesis route for 2,5-dioxane-1,4-diones.

DETAILED DESCRIPTION OF THE INVENTION

Figure 1:
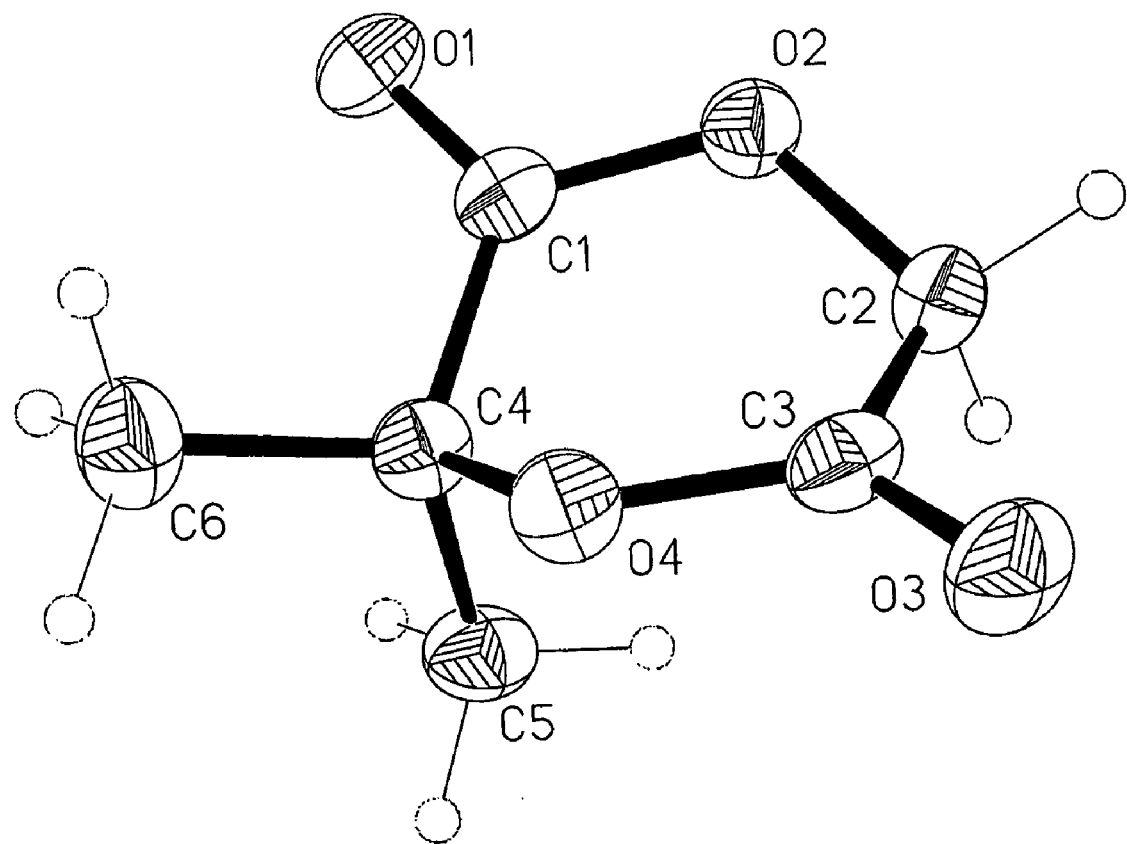
FIG. 1 is a crystal structure of 3,3-dimethyl-2,5-dioxane-1,4-dione synthesized according to Example 1.

As subject of the present invention is therefore a process for preparing 2,5-dioxane-1,4-diones of formula (I)

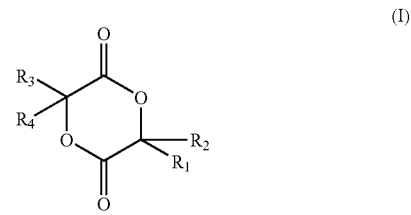

in which $R_1$, $R_2$, $R_3$ and $R_4$ represent, independently, the hydrogen atom; halo; ($C_2$-$C_6$)alkenyl; ($C_3$-$C_7$)cycloalkyl; cyclohexenyl; a radical of formula —$(CH_2)_m$—V—W
    V represents a covalent bond, the oxygen atom or the —C(O)—O— radical;
    W represents the hydrogen atom, a ($C_1$-$C_{18}$)alkyl radical optionally substituted by one or more identical or different halo radicals; the aryl or aralkyl radical, the aryl and aralkyl radicals being optionally substituted by one or more identical or different substituents chosen from: —$(CH_2)_n$—Y-Z, halo, nitro and cyano;
    Y represents —O—, —S— or a covalent bond;
    Z represents the hydrogen atom or a ($C_1$-$C_6$)alkyl radical optionally substituted by one or more identical or different halo radicals; or aralkyl;
    m and n represent independently an integer from 0 to 4;

by oxidation of the ketone function of a cyclic compound of formula (II)

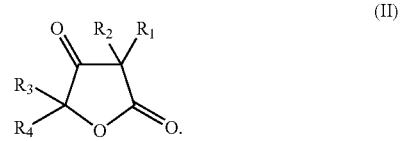

In the definitions indicated above, the expression halo represents the fluoro, chloro, bromo or iodo radical, preferably chloro, fluoro or bromo. The expression ($C_1$-$C_6$)alkyl represents a linear or branched alkyl radical having from 1 to 6 carbon atoms, such as the methyl, ethyl, propyl, isopropyl, butyl, isobutyl, sec-butyl and tert-butyl, pentyl or amyl, isopentyl, neopentyl, 2,2-dimethyl-propyl, hexyl, isohexyl or 1,2,2-trimethyl-propyl radicals. The term ($C_1$-$C_{18}$)alkyl designates a linear or branched alkyl radical having 1 to 18 carbon atoms, such as the radicals containing from 1 to 6 carbon atoms as defined above but also heptyl, octyl, 1,1,2,2-tetramethyl-propyl, 1,1,3,3-tetramethyl-butyl, nonyl, decyl, undecyl, dodecyl, tridecyl, tetradecyl, pentadecyl, hexadecyl, heptadecyl, octadecyl. By the expression alkyl substituted by at least one radical halo is meant any linear or branched alkyl chain, containing at least one radical halo positioned along the chain such as for example —CHCl—CH$_3$ but also —CF$_3$.

In the present Application also, the (CH$_2$)$_i$ radical (i being an integer which can represent m and n as defined above), represents a linear or branched hydrocarbonated chain, of i carbon atoms. Thus the —(CH$_2$)$_3$— radical can represent —CH$_2$—CH$_2$—CH$_2$— but also —CH(CH$_3$)—CH$_2$—, —CH$_2$—CH(CH$_3$)— or —C(CH$_3$)$_2$—.

By (C$_2$-C$_6$)alkenyl, is meant a linear or branched alkyl radical containing from 2 to 6 carbon atoms and having at least one unsaturation (double bond), such as for example vinyl, allyl, propenyl, butenyl or pentenyl.

The term (C$_3$-C$_7$)cycloalkyl designates a saturated carbon monocyclic system comprising from 3 to 7 carbon atoms, and preferably the cyclopropyl, cyclobutyl, cyclopentyl, cyclohexyl or cycloheptyl rings.

The expression aryl represents an aromatic radical, constituted by a condensed ring or rings, such as for example the phenyl, naphthyl, fluorenyl or anthryl radical. The term aralkyl (arylalky) preferably designates the radicals in which the aryl and alkyl radicals are as defined above such as for example benzyl or phenethyl.

Thus, during the conversion process of compound (II) to compound (I)

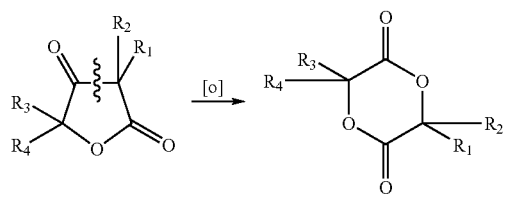

the competitive dimerization and oligomerization reactions which are observed during the synthesis of lactide or glycolide by condensation, are completely avoided.

For conversion of the ketone function of compound (II) to an ester function, several types of oxidation can be utilized; the oxidation can thus be carried out for example in the presence of an oxidizing agent such as a peracid or a peroxide (according to the Baeyer Villiger oxidation reaction), in the presence of a metallic catalyst (S. I. Murahashi et al., *Tetrahedron Lett.* 1992, 33, 7557-7760 and C. Bolm et al., *Tetrahedron Lett.* 1993, 34, 3405-3408) or by enzymatic route (M. D. Mihovilovic et al., *Eur. J. Org. Chem.* 2002, 3711-3730).

Preferably, a process according to the invention is carried out in the presence of an oxidizing agent according to the Baeyer Villiger oxidation reaction. In this case, the oxidation reaction is carried out very preferentially on the more encumbered side of the ketone in such a manner that 2,5-dioxane-1,4-diones can be obtained very selectively. In a preferable way, the oxidizing agent is used in the presence of a catalyst.

The oxidizing agent (or oxidation agent) used for implementing the process according to the invention, can be a peracid or a peroxide. As an example of a peracid, there can be mentioned trifluoroperacetic acid (TFPAA), peracetic acid (PAA), metachloroperbenzoic acid (m-CPBA), preferably in combination with Lewis acids (SnCL$_4$, Sn(OTf)$_3$, Re(OTf)$_3$) or strong acids (sulphonic acids, Nafion-H, CF$_3$COOH etc.). As an example of a peroxide, there can be mentioned hydrogen peroxide (H$_2$O$_2$); the hydrogen peroxide is used alone or in the presence of a catalyst which can be a Lewis acid (such as BF$_3$) or a metallic complex either in homogeneous phase (Mo, Re, Pt) or in heterogeneous phase (tin zeolite, tin hydrotalcite); there can also be mentioned bis(trimethylsilyl)peroxide Me$_3$SiOOSiMe$_3$ which is used in the presence of a Lewis acid (Me$_3$SiOTf, SnCl$_4$ or BF$_3$·OEt$_2$).

A more particular subject of the present invention is a process as defined above, characterized in that the oxidation agent is a peracid or a peroxide.

Preferably, the oxidizing agent is a peracid. The peracid is preferably used in the presence of a Lewis acid or a strong acid, and more particularly in presence of a strong acid selected from sulphonic acids.

More preferably the peracid is metachloroperbenzoic acid (m-CPBA). The metachloroperbenzoic acid is preferably used in the presence of trifluoromethanesulfonic acid.

Preferably also, the oxidizing agent is a peroxide.

The oxidation agents mentioned above are in general commercially available. The non-commercial agents can be synthesized according to methods known to a person skilled in the art. Thus, trifluoroperacetic acid which is not commercial can be easily obtained by the action of hydrogen peroxide H$_2$O$_2$ on trifluoroacetic acid or anhydride CF$_3$CO$_2$H and (CF$_3$CO)$_2$O respectively (R. Liotta et al., *J. Org. Chem.* 1980, 45, 2887-2890; M. Anastasia et al., *J. Org. Chem.* 1985, 50, 321-325; P. A. Krasutsky et al., *J. Org. Chem.* 2001, 66, 1701-1707). Similarly, bis(trimethylsilyl)peroxide is not commercially available but it is easily accessible from the H$_2$O$_2$-1,4-diazabicyclo[2,2,2]octane [DABCO, N(CH$_2$CH$_2$)$_3$N] and Me$_3$SiCl complex (P. G. Cookson e al., *J. Organomet. Chem.* 1975, 99, C31-C32; M. Taddei et al., *Synth. Comm.* 1986, 633-635).

The cyclic keto-esters of formula (II), used as precursors for the synthesis of 2,5-dioxane-1,4-diones (I) as defined above, are easily accessible by standard methods known to a person skilled in the art (E. B. Reid et al., *J. Org. Chem.* 1950, 15, 572-582).

A more particular subject of the present invention is also a process as defined above, characterized in that the aryl radical is the phenyl radial and the aralkyl radical is the benzyl radical.

A more particular subject of the present invention is also a process as defined above, characterized in that R$_1$, R$_2$, R$_3$ and R$_4$ represent, independently, the hydrogen atom; or a radical of formula —(CH$_2$)$_m$—V—W with V which represents a covalent bond and W a (C$_1$-C$_6$)alkyl radical, and preferably R$_1$, R$_2$, R$_3$ and R$_4$ represent, independently, the hydrogen atom, the methyl radical or the ethyl radical.

A more particular subject of the present invention is also a process as defined above, characterized in that R$_1$ and R$_2$ represent, independently, a radical of formula —(CH$_2$)$_m$—V—W with V which represents a covalent bond, m=0 and W a (C$_1$-C$_6$)alkyl radical, and R$_3$ and R$_4$ represent, independently, the hydrogen atom or a radical of formula —(CH$_2$)$_m$—V—W with V which represents a covalent bond, m=0 and W a (C$_1$-C$_6$)alkyl radical.

A more particular subject of the present invention is also a process as defined above, characterized in that R$_1$ and R$_2$ represent, independently, the methyl or ethyl radical, and R$_3$ and R$_4$ represent, independently, the hydrogen atom, the methyl or ethyl radical.

A subject of the present invention is also compounds of formula (I) as obtained according to the method defined above.

Experimental Part

EXAMPLE 1

3,3-dimethyl-2,5-dioxane-1,4-dione

Stage 1: Synthesis of the Precursor (II)

The synthesis of compound (II) is carried out according to the following reaction diagram:

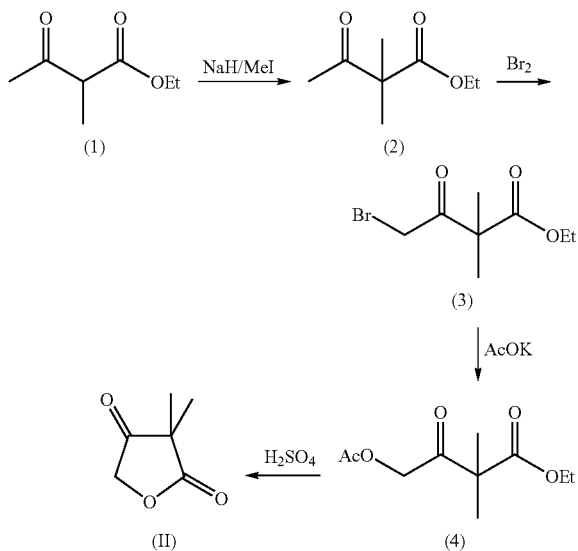

The formation of compound (2) from compound (1) can be carried out according to H. C. Brown et al., *J. Am. Chem. Soc.* 1988, 110, 1539-1546. The synthesis stages of compounds (3) and (4) can be carried out according to M. Conrad et al., *Ber.* 1898, 31, 2726-2731. Finally, the final stage of formation of compound (II) from compound (4) can be carried out according to E. B. Reid et al., *J. Org. Chem.* 1950, 15, 572-582.

Stage 2: Synthesis of 3,3-dimethyl-2,5-dioxane-1,4-dione

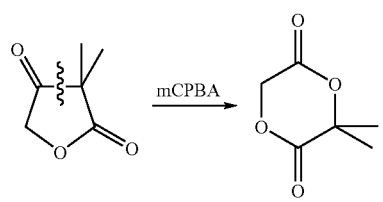

Conditions 1:

A solution of 5 g of cyclic keto-ester (39 mmol) and 13.5 g of metachloropebenzoic acid (2 eq.) in 100 ml of dichloromethane is heated under reflux for 48 hours. NMR $^1$H monitoring of an aliquot of the reaction medium reveals the complete conversion of the ring with 5 members and the formation of mostly 3,3-dimethyl-2,5-dioxane-1,4-dione (spectroscopic yield: 85%).

Conditions 2:

A solution of 5 g of cyclic keto-ester (39 mmol) and 8.1 g of metachloroperbenzoic acid (1.2 eq.) in 40 ml of dichloromethane is heated under reflux for 24 hours. The complete conversion of the ring with 5 members is monitored by NMR $^1$H on a sample. The reaction medium is then cooled down to −18° C. overnight then filtered on frit in order to eliminate the metachlorobenzoic acid formed. The filtrate is concentrated under vacuum. The residue is recrystallized from ethyl acetate at −18° C. 3.9 g of analytically pure, 3,3-dimethyl-2,5-dioxane-1,4-dione are thus obtained (70% of isolated product yield). The product is characterized by NMR $^1$H [4.97 (s, 2H), 1.70 (s, 6H)] and $^{13}$C [167.7 and 163.9 (C=O), 79.8 ($C_q$), 65.8 ($CH_2$), 25.8 ($CH_3$)], RX (cf. FIG. 1), mp (84-85° C.) and elementary analysis. Calculated C: 50.00, H: 5.56. Found C: 49.98, H: 5.33.

Conditions 3:

A solution of 1 g of cyclic keto-ester (7.8 mmol), 2.7 g of metachloroperbenzoic acid (2 eq.) and 70 μl of trifluoromethanesulphonic acid (0.1 eq.) in 20 ml of dichloromethane is left under stirring at ambient temperature for 3 hours. The solvent is eliminated under vacuum, then the medium is analyzed. NMR $^1$H reveals the complete conversion of the ring with 5 members and the formation of mostly 3,3-dimethyl-2,5-dioxane-1,4-dione (spectroscopic yield: 60%).

EXAMPLE 2

3-ethyl-3-methyl-2,5-dioxane-1,4-dione

Stage 1: Synthesis of Precursor (II)

The synthesis of compound (II) is carried out according to the same reaction diagram as in Example 1:

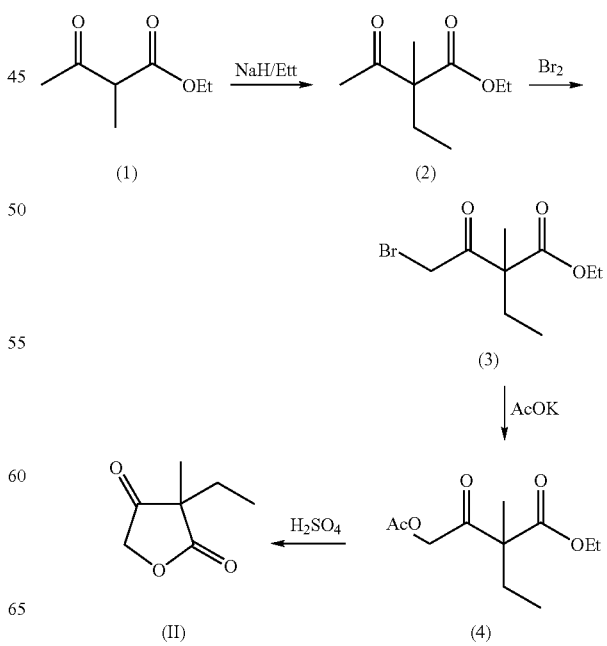

Stage 2: Synthesis of
3-ethyl-3-methyl-2,5-dioxane-1,4-dione

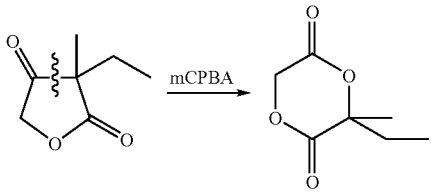

A solution of 0.5 g of cyclic keto-ester (3.5 mmol) and 1.21 g of metachloroperbenzoic acid (2 eq.) in 10 ml of dichloromethane is heated under reflux for 48 hours. After returning to ambient temperature, the solvent is eliminated under vacuum. NMR $^1$H analysis reveals the complete conversion of the ring with 5 members and the formation of mostly 3-ethyl-3-methyl-2,5-dioxane-1,4-dione (spectroscopic yield: 75%). NMR $^1$H characteristics [4.97 (s, 2H), 1.95 (q, 2H, $^3J_{HH}$=7.5 Hz), 1.67 (s, 3H), 1.03 (t, 3H, $^3J_{HH}$=7.5 Hz)].

TABLE 1

Crystallographic data of the compound of the example 1.

| | |
|---|---|
| Empirical formula | C6 H8 O4 |
| Molar mass | 144.12 |
| Temperature | 193(2) K |
| Wavelength | 0.71073 Å |
| Crystalline system | Orthorhombic |
| Space group | P2(1)2(1)2(1) |
| Lattice parameters | a = 5.8935(10) Å   α = 90°. |
| | b = 9.6410(16) Å   β = 90°. |
| | c = 11.6372(19) Å   γ = 90°. |
| Volume | 661.22(19) Å$^3$ |
| Z | 4 |
| Density (calculated) | 1.448 Mg/m$^3$ |
| Absorption coefficient | 0.123 mm$^{-1}$ |
| F(000) | 304 |
| Crystal size | 0.2 × 0.2 × 0.6 mm$^3$ |
| Theta values for data acquisition | from 2.74 to 26.38°. |
| Values of the indices h, k, l | −7 <= h <= 4, −12 <= k <= 12, −14 <= l <= 14 |
| Collected reflections | 4337 |
| Independent reflections | 1346 [R(int) = 0.0559] |
| Coll./the. data ratio up to theta 26.38° | 100.0% |
| Absorption correction | None |
| Refinement method | Full matrix least squares on F$^2$ |
| Data/constraints/parameters | 1346/0/93 |
| Correlation coefficient on F$^2$ | 1.070 |
| Final R indices [I > 2sigma(I)] | R1 = 0.0308, wR2 = 0.0742 |
| R indices (all data) | R1 = 0.0364, wR2 = 0.0774 |
| Absolute structural parameter | 0.2(12) |
| Max and min residual elec. density | 0.182 and −0.144 e.Å$^{-3}$ |

TABLE 2

Atomic coodinates (×10$^4$) and equivalent isotropic displacement parameters (Å$^2$ × 10$^3$). U(eq) is defined as one-third trace of the orthogonalized tensor U$^{ij}$ of the compound of the example 1.

| | x | y | z | U(eq) |
|---|---|---|---|---|
| C(1) | 1812(2) | 3446(2) | 10097(1) | 25(1) |
| O(1) | 2005(2) | 3662(1) | 11125(1) | 32(1) |
| C(2) | 1817(3) | 2391(2) | 8227(1) | 30(1) |
| O(2) | 1915(2) | 2288(1) | 9464(1) | 28(1) |
| C(3) | 320(3) | 3535(2) | 7795(1) | 28(1) |
| O(3) | −557(2) | 3507(1) | 6861(1) | 39(1) |
| C(4) | 1500(2) | 4820(2) | 9471(1) | 26(1) |
| O(4) | −18(2) | 4628(1) | 8487(1) | 29(1) |
| C(5) | 3794(3) | 5354(2) | 9049(1) | 35(1) |
| C(6) | 310(3) | 5865(2) | 10226(1) | 37(1) |

TABLE 3

Bond lengths [Å] and bond angles [°] of the compound of the example 1.

| | |
|---|---|
| C(1)—O(1) | 1.2047(17) |
| C(1)—O(2) | 1.3391(19) |
| C(1)—C(4) | 1.523(2) |
| C(2)—O(2) | 1.4435(16) |
| C(2)—C(3) | 1.499(2) |
| C(3)—O(3) | 1.2033(18) |
| C(3)—O(4) | 1.3412(19) |
| C(4)—O(4) | 1.4643(18) |
| C(4)—C(6) | 1.510(2) |
| C(4)—C(5) | 1.528(2) |
| O(1)—C(1)—O(2) | 119.12(14) |
| O(1)—C(1)—C(4) | 123.02(14) |
| O(2)—C(1)—C(4) | 117.85(12) |
| O(2)—C(2)—C(3) | 114.11(12) |
| C(1)—O(2)—C(2) | 119.30(12) |
| O(3)—C(3)—O(4) | 119.77(15) |
| O(3)—C(3)—C(2) | 122.60(14) |
| O(4)—C(3)—C(2) | 117.63(12) |
| O(4)—C(4)—C(6) | 104.80(12) |
| O(4)—C(4)—C(1) | 109.75(12) |
| C(6)—C(4)—C(1) | 110.98(13) |
| O(4)—C(4)—C(5) | 109.40(12) |
| C(6)—C(4)—C(5) | 111.91(14) |
| C(1)—C(4)—C(5) | 109.88(12) |
| C(3)—O(4)—C(4) | 118.55(12) |

TABLE 4

Anisotropic displacement parameters (Å$^2$ × 10$^3$) of the compound of the example 1. The anisotropic displacement factor exponent takes the form: $-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| C(1) | 16(1) | 33(1) | 26(1) | 2(1) | −1(1) | 0(1) |
| O(1) | 29(1) | 45(1) | 23(1) | 5(1) | −2(1) | 2(1) |
| C(2) | 33(1) | 33(1) | 24(1) | −3(1) | 0(1) | 1(1) |
| O(2) | 30(1) | 29(1) | 25(1) | 2(1) | −2(1) | 2(1) |
| C(3) | 25(1) | 36(1) | 23(1) | 3(1) | 0(1) | −5(1) |
| O(3) | 44(1) | 48(1) | 25(1) | 0(1) | −8(1) | −2(1) |
| C(4) | 25(1) | 30(1) | 23(1) | 1(1) | −4(1) | 0(1) |
| O(4) | 30(1) | 30(1) | 27(1) | 2(1) | −7(1) | 3(1) |
| C(5) | 33(1) | 36(1) | 34(1) | 3(1) | −2(1) | −10(1) |
| C(6) | 41(1) | 36(1) | 35(1) | −4(1) | −3(1) | 9(1) |

TABLE 5

Coordinates of the hydrogen atoms (×10$^4$) and isotropic displacement parameters (Å$^2$ × 10$^3$) of the compound of the example 1.

| | x | y | z | U(eq) |
|---|---|---|---|---|
| H(2A) | 1262 | 1499 | 7913 | 36 |
| H(2B) | 3372 | 2540 | 7930 | 36 |
| H(5A) | 4514 | 4648 | 8565 | 52 |
| H(5B) | 4770 | 5554 | 9710 | 52 |

TABLE 5-continued

Coordinates of the hydrogen atoms (×10⁴) and isotropic displacement parameters (Å² × 10³) of the compound of the example 1.

|      | x     | y    | z     | U(eq) |
|------|-------|------|-------|-------|
| H(5C)| 3570  | 6203 | 8600  | 52    |
| H(6A)| 58    | 6723 | 9792  | 56    |
| H(6B)| 1252  | 6064 | 10900 | 56    |
| H(6C)| −1153 | 5487 | 10476 | 56    |

The invention claimed is:

1. Process for the preparation of 2,5-dioxane-1,4-diones of formula (I)

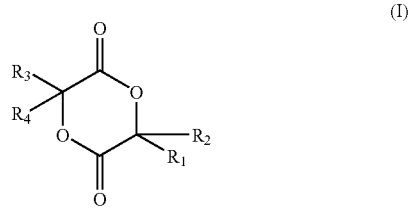

in which $R_1$, $R_2$, $R_3$ and $R_4$ are, independently, a hydrogen atom; halo; $(C_2-C_6)$ alkenyl; $(C_3-C_7)$ cycloalkyl; cyclohexenyl; or a radical of formula $-(CH_2)_m-V-W$; wherein V is a covalent bond, an oxygen atom or a $-C(O)-O-$ radical;

W is a hydrogen atom, a $(C_1-C_{18})$ alkyl radical optionally substituted by one or more identical or different halo radicals; an aryl or aralkyl radical, the aryl and aralkyl radicals being optionally substituted by one or more identical or different substituents including: $-(CH_2)_n-Y-Z$, halo, nitro or cyano;

Y is $-O-$, $-S-$ or a covalent bond;

Z is a hydrogen atom or a $(C_1-C_6)$ alkyl radical optionally substituted by one or more identical or different halo radicals; or aralkyl;

m and n are independently an integer from 0 to 4;

comprising oxidizing the ketone function of a cyclic compound of formula (II)

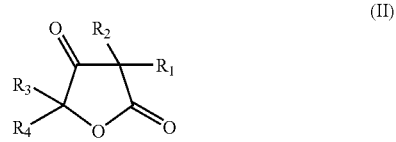

in which $R_1$, $R_2$, $R_3$ and $R_4$ are defined above, wherein the oxidizing is carried out in the presence of a peracid as an oxidizing agent and in the presence of a sulfonic acid as a catalyst.

2. Preparation process according to claim 1, wherein the oxidizing agent is metachloroperbenzoic acid.

3. Preparation process according to claim 2, wherein the oxidizing agent is used in the presence of trifluoromethanesulfonic acid.

4. Preparation process according to claim 1, wherein the aryl radical is a phenyl radical and the aralkyl radical is a benzyl radical.

5. Preparation process according to claim 1, wherein $R_1$, $R_2$, $R_3$ and $R_4$ are, independently, a hydrogen atom or a radical of formula $-(CH_2)_m-V-W$, wherein V is a covalent bond and W is a $(C_1-C_6)$ alkyl radical.

6. Preparation process according to claim 1, wherein $R_1$, $R_2$, $R_3$ and $R_4$ are, independently, a hydrogen atom, a methyl or ethyl radical.

7. Preparation process according to claim 1, wherein $R_1$ and $R_2$ are, independently, a radical of formula $-(CH_2)_m-V-W$, wherein V is a covalent bond, m=0 and W is a $(C_1-C_6)$ alkyl radical, and $R_3$ and $R_4$ are, independently, a hydrogen atom or a radical of formula $-(CH_2)_m-V-W$, wherein V is a covalent bond, m=0 and W is a $(C_1-C_6)$ alkyl radical.

8. Preparation process according to claim 1, wherein $R_1$ and $R_2$ are, independently, a methyl or ethyl radical, and $R_3$ and $R_4$ are, independently, a hydrogen atom, a methyl or ethyl radical.

* * * * *